United States Patent
Sanderford

(10) Patent No.: US 10,898,710 B1
(45) Date of Patent: Jan. 26, 2021

(54) INVOLUNTARY RESPONSE STIMULATOR AND THERAPY

(71) Applicant: Bergen Sanderford, New Orleans, LA (US)

(72) Inventor: Bergen Sanderford, New Orleans, LA (US)

( * ) Notice: Subject to any disclaimer, the term of this patent is extended or adjusted under 35 U.S.C. 154(b) by 87 days.

(21) Appl. No.: 15/926,975

(22) Filed: Mar. 20, 2018

Related U.S. Application Data

(60) Provisional application No. 62/474,003, filed on Mar. 20, 2017.

(51) Int. Cl.
*A61B 5/00* (2006.01)
*A61N 1/36* (2006.01)
*G01N 33/50* (2006.01)

(52) U.S. Cl.
CPC ........ *A61N 1/36014* (2013.01); *A61B 5/4082* (2013.01); *A61B 5/7278* (2013.01); *G01N 33/5058* (2013.01)

(58) Field of Classification Search
CPC .......... A61N 1/36014; A61B 5/4082; A61B 5/7278; G01N 33/5058
USPC ......................................... 434/262
See application file for complete search history.

(56) References Cited

U.S. PATENT DOCUMENTS

| | | | |
|---|---|---|---|
| 4,842,607 A | 6/1989 | Repperger et al. | |
| 6,458,089 B1 | 10/2002 | Ziv-Av | |
| 6,695,794 B2 | 2/2004 | Kaiser et al. | |
| 9,067,098 B2 | 6/2015 | Alberts | |
| 2003/0125781 A1* | 7/2003 | Dohno | A63B 21/00181 607/75 |
| 2014/0336539 A1 | 11/2014 | Torres et al. | |
| 2015/0272807 A1 | 10/2015 | Gupta et al. | |
| 2017/0014625 A1 | 1/2017 | Rosenbluth et al. | |

FOREIGN PATENT DOCUMENTS

CN 104440920 A 3/2013

OTHER PUBLICATIONS

Immel, Sebastian R, et al. 'A Physical Hand Tremor Simulator for Use With Inclusive Design Research'. Mar. 13, 2015; pp. 1-8; https://asmedigitalcollection.asme.org/IMECE/proceedings/IMECE2014/46606/V011T14A025/260920 (Year: 2015).*
Sandrine Ceurstemont, "What it's like to have Parkinson's for 15 minutes." https://www.newscientist.com/article/dn26589-what-its-like-to-have-parkinsons-for-15-minutes/. Nov. 19, 2014.
"Raspberry Pi-Powered Body Illusion Lets You Experience Parkinson's." https://science.slashdot.org/story/14/11/25/0018244/raspberry-pi-powered-body-illusion-lets-you-experience-parkinsons. Nov. 24, 2014.
Susie East, "Could this glove be the solution to Parkinson's tremors?" http://www.cnn.com/2016/02/16/health/gyroglove-parkinsons-tremors-feat/. Feb. 16, 2016.

* cited by examiner

*Primary Examiner* — Robert P Bullington
(74) *Attorney, Agent, or Firm* — Olive Law Group, PLLC; Ronald A. Rudder

(57) ABSTRACT

An apparatus for simulating hand tremors caused by Essential Tremor and Parkinson's disease which may also be used as part of a therapeutic program in association with surgically implanted stem cells introduced into a patient's substantia nigra.

22 Claims, 7 Drawing Sheets

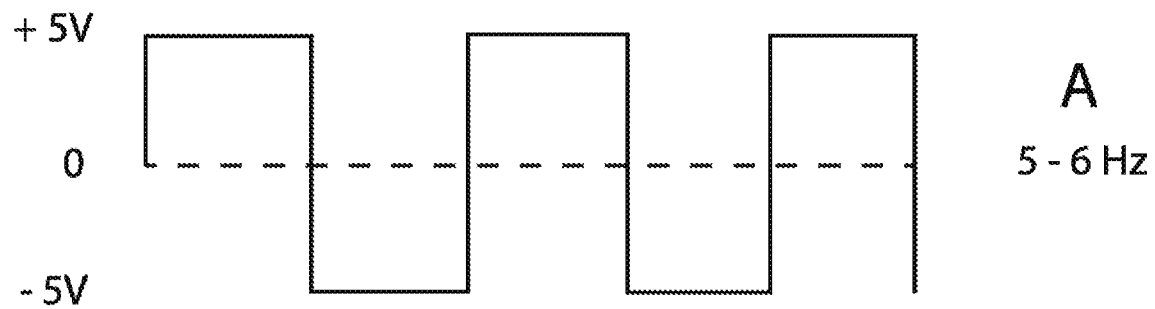
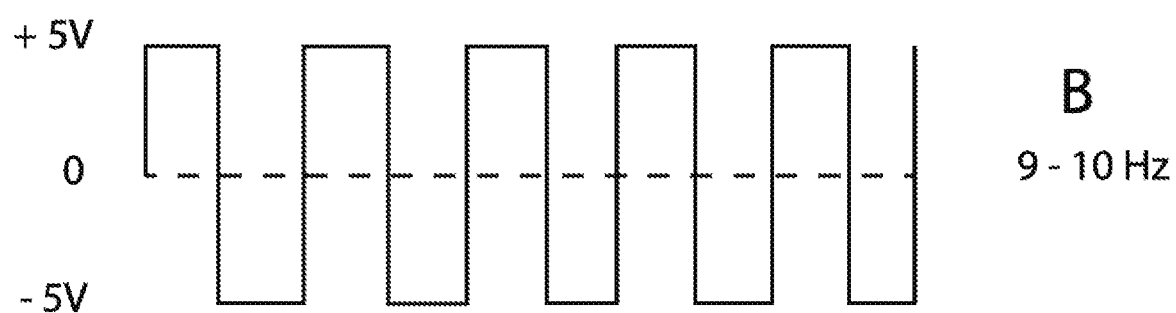
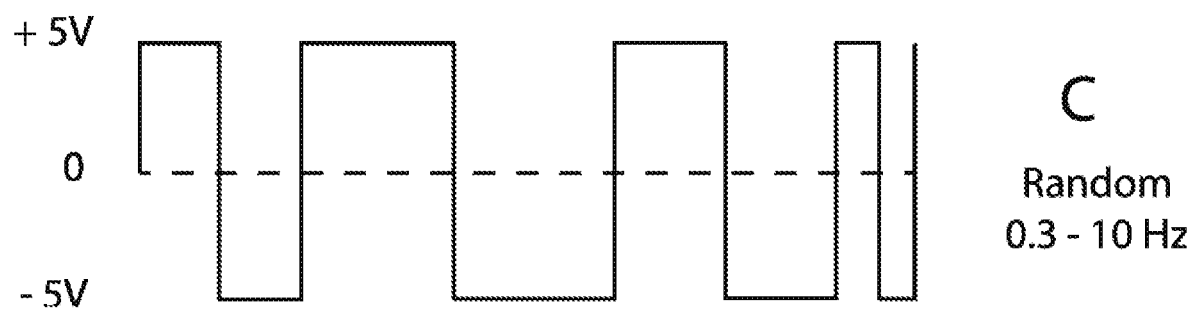
FIG. 3

INVOLUNTARY RESPONSE STIMULATOR AND THERAPY

BACKGROUND OF THE INVENTION

I. Field of the Invention

The present invention relates generally to a mechanism for simulation, and a method of therapy using said mechanism, to reduce symptoms of Parkinson's disease (PD) or Essential Tremors (ET).

II. General Background

PD is caused by the degeneration of dopamine neurons in the substantia nigra, a part of the basal ganglia (area that controls movements). It is in the midbrain not the cortex. Neurons in the substantia nigra inhibit the shaking (abnormal) movements. Parkinson's' develops when 80-90% of those neurons in the substantia nigra die, removing the normal inhibition on the abnormal movement. The only existing treatment is to boost the activity of the surviving nigral neurons by taking a medicine that increases the amount of dopamine (the chemical that these cells use to transmit signals) in the nerve cells. The medicine is called L-dopa and is used by the nerve cells to make more dopamine signal. This works rather well until so many nerve cells die that the substantia nigra is essentially gone, usually 20-30 years. L-dopa also causes side effects such as sleeplessness.

"The key assumption of this model is that (single) thalamic neurons, not that basal ganglia circuitry, form the tremor pacemaker. This hypothesis is based on in vitro preparations of guinea pig thalamic neurons, where it was found that the intrinsic biophysical properties of thalamic neurons allow them to serve as relay systems and as single cell oscillators at two distinct frequencies, 9-10 Hz and 5-6 Hz. Specifically, slightly depolarized thalamic cells tend to oscillate at 10 Hz, whereas hyperpolarized cells oscillate at 6 Hz. These two frequencies coincide with the frequency of physiological tremor and PD tremor, respectively. However, in vivo measurements in the thalamus of PD patients have questioned the presence of these thalamic pacemaker cells. That is, although 6 Hz oscillatory mode in the animal model is associated with low-threshold calcium spike bursts, this pattern was not observed (with a rare exception in the thalamus of PD patients with tremor." Excerpt from Rick C Helmich et al., "The Pathophysiology of Essential Tremor and Parkinson's Tremor", 27 Jul. 2013, Neuroimaging.

"ET and PD resting tremor are both associated with oscillatory activity in the cerebellothalamocortical circuit. Network parameters such as within-circuit or between circuit connectivity may explain both differences and overlap between tremors, and they can be used to improve existing tremor therapies." Excerpt from Rick C Helmich et al., "The Pathophysiology of Essential Tremor and Parkinson's Tremor", 27 Jul. 2013, Neuroimaging.

Dopamine is a neuro transmitter that is naturally released in the brain to reinforce learning. In a heathy individual, Dopamine production is the greatest when a predicted result has a reduced error compared to actual results, but importantly, Dopamine levels then reduce to zero as the error reduces to zero. This curve encourages learning of new environmental stimulus, but once learned (i.e., once the error nears zero) re-enforcement is no longer needed.

It is speculated that stem cells can be introduced into the mature brain and will differentiate into neurons similar to those in physical proximity. However, these cells will likely die in one to two weeks unless they become integrated into local neural wiring (connections between dendrites and axons). Further, in order for the new neuron to remain viable it must fire in synchronization with other local neurons. The general wisdom is that neurons that fire together, wire together. It is speculated that this can happen naturally or can be enhanced by an external stimulus.

In the past, therapies involving pens with gyroscopes or shock therapy were employed. There is a need for an inexpensive device which both simulates involuntary tremors and also allows for therapeutic retraining of neuros in those with ET and PD.

SUMMARY OF THE INVENTION

In accordance with one embodiment, the present invention is an apparatus for simulating hand tremors comprising, comprising: a waveform generator operable to output a waveform; an electric driver connected to said waveform generator, wherein said electric driver is operable to receive as an input said waveform, and wherein said electric driver outputs a drive signal, wherein said drive signal varies in response to changes in said waveform; an actuator comprising a connection point, wherein said actuator is connected to said electric driver, wherein said actuator is operable to receive as an input said drive signal, and wherein said actuator is operable to displace said connection point along an axis in response to said drive signal; a cuff configured to encircle a portion of a human hand or arm; and a connecting mechanism attached to said connection point and to said cuff; wherein operation of said actuator displaces said cuff along said axis.

In another embodiment, the present invention is an apparatus for providing physical therapy to an individual, said apparatus comprising: a waveform generator operable to output a waveform; an electric driver connected to said waveform generator, wherein said electric driver is operable to receive as an input said waveform, and wherein said electric driver outputs a drive signal, wherein said drive signal varies in response to changes in said waveform; an actuator comprising a connection point, wherein said actuator is connected to said electric driver, wherein said actuator is operable to receive as an input said drive signal, and wherein said actuator is operable to displace said connection point along an axis in response to said drive signal; a cuff configured to encircle a portion of a hand or arm of said individual, wherein operation of said actuator displaces said cuff along said axis; a connecting mechanism attached to said connection point and to said cuff; a means for monitoring a dopamine level of said individual when said individual's hand or arm is placed inside of said cuff and said apparatus in in operation, wherein said monitoring means generates a monitoring means output; and a control system connected to said monitoring means, wherein said monitoring means output is an input to said control system, wherein said control system is connected to said waveform generator, and wherein said control system is operable to modify the amplitude and frequency of said waveform to maximize said dopamine level of said individual during use of said apparatus.

The present invention further embodies a method of providing physical therapy session to a patient who has had undifferentiated or differentiated stem cells surgically introduced into said patient's substantia nigra, said method comprising: providing a therapeutic apparatus, said therapeutic apparatus comprising: a waveform generator operable to output a waveform; an electric driver connected to said waveform generator, wherein said electric driver is operable to receive as an input said waveform, and wherein said electric driver outputs a drive signal, wherein said drive signal varies in response to changes in said waveform; an actuator comprising a connection point, wherein said actuator is connected to said electric driver, wherein said actuator is operable to receive as an input said drive signal, and wherein said actuator is operable to displace said connection point along an axis in response to said drive signal; a cuff configured to encircle a portion of said patient's hand or arm, wherein operation of said actuator displaces said cuff along said axis; and a connecting mechanism attached to said connection point and to said cuff; a means for monitoring a dopamine level of said patient when said patient's hand or arm is placed inside of said cuff and said apparatus in in operation, wherein said monitoring means generates a monitoring means output; and a control system connected to said monitoring means, wherein said monitoring means output is an input to said control system, wherein said control system is connected to said waveform generator, and wherein said control system is operable to modify the amplitude and frequency of said waveform to maximize said dopamine level of said individual during use of said apparatus; securing a wrist or arm of said patient into said cuff; activating said apparatus such that said cuff exerts a reciprocating opposing force to said patient's hand; instructing said patient to attempt a repetitive hand-eye coordinated task with said hand secured in said cuff; monitoring said patient's dopamine levels using said monitoring means while said patient attempts said repetitive hand-eye coordinated task; and, modifying said waveform using said control system in response to said monitoring means output to maximize said patient's dopamine levels during said therapy session.

BRIEF DESCRIPTION OF THE DRAWINGS

The foregoing and other objects, features, and advantages of the invention are apparent from the following detailed description taken in conjunction with the accompanying drawings in which like parts are given like reference numerals and, wherein:

FIG. 3 shows three exemplary drive signals output by the Controllable Waveform Generator of FIG. 2.

Figure 1:
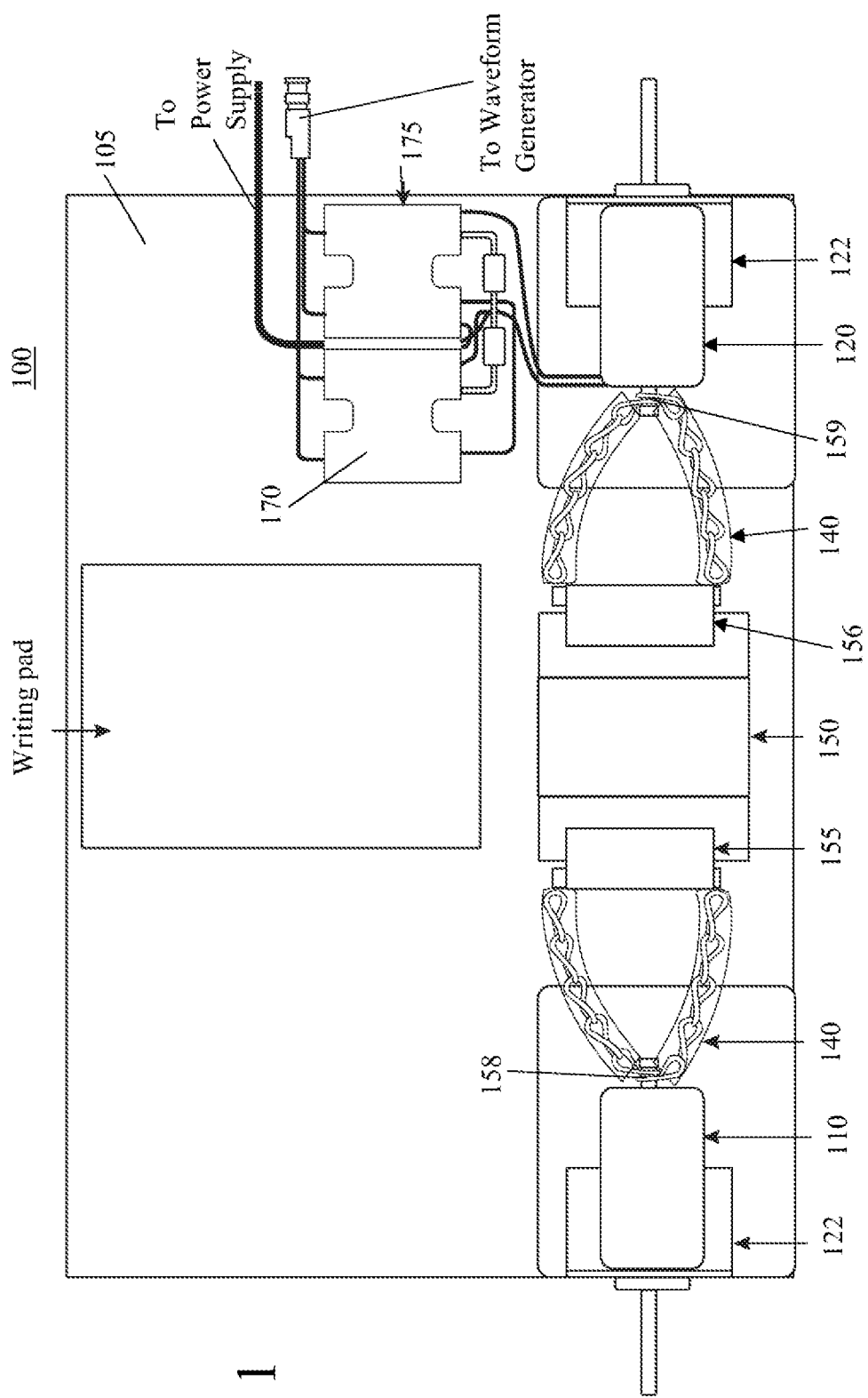
FIG. 1 depicts an embodiment of an apparatus for simulating certain neurologically-caused hand tremors.

The images in the drawings are simplified for illustrative purposes and are not depicted to scale. Within the descriptions of the figures, similar elements are provided similar names and reference numerals as those of the previous figure(s). The specific numerals assigned to the elements are provided solely to aid in the description and are not meant to imply any limitations (structural or functional) on the invention.

The appended drawings illustrate exemplary configurations of the invention and, as such, should not be considered as limiting the scope of the invention that may admit to other equally effective configurations. It is contemplated that features of one configuration may be beneficially incorporated in other configurations without further recitation.

DETAILED DESCRIPTION

The embodiments of the disclosure will be best understood by reference to the drawings, wherein like parts are designated by like numerals throughout. It will be readily understood that the components, as generally described and illustrated in the Figures herein, could be arranged and designed in a wide variety of different configurations or be entirely separate. Thus, the following more detailed description of the embodiments of the system and method of the disclosure, as represented in the Figures is not intended to limit the scope of the disclosure, as claimed, but is merely representative of possible embodiments of the disclosure.

FIG. 1 shows tremor simulator device 100, which has two actuators 110 and 120 on either side of a plush cuff 150. Cuff 150 may be made from plastic or any other suitably strong material. Cuff 150 may be lined with a soft pad 151, such as plush foam, for safety and comfort when patient inserts their hand into cuff 150. Actuators 110 and 120 are mounted to mounting brackets 122, which are in turn attached to a base 105, such that actuators 110 and 120 are located on opposite sides of cuff 150. Actuators 110 and 120 include connection points 158 and 159, respectively. In one embodiment, actuators 110 and 120 are electromagnetic actuators such as solenoids. Said actuators can alternatively be pneumatic actuators, reciprocating motors, voice coils, or the like.

Connectors 152 and 153 are located on, and attached to, opposite sides of cuff 150. Connector 152 is connected to actuator 110 at connection point 158 by a pair of semi-rigid connecting mechanisms 140. Connector 153 is likewise connected to actuator 120 at connection point 159 by a similar pair of semi-rigid connecting mechanisms 140. In an embodiment, semi-rigid connecting mechanisms 140 comprise a metallic chain link 141 encased in elastic tube 142 (where elastic tube 142 can be made of plastic, rubber, or similar material). In alternative embodiments, semi-rigid connecting mechanisms 140 may comprise metallic link chain, partially elastic plastic/rubber tube, sliding rail, or similar connecting mechanisms.

In an embodiment, a pair of drivers 170 and 175 apply power to actuators 110 and 120. In an embodiment, drivers 170 and 175 may be opto-isolators, transistors protected by a fly back diode, or relays. Actuators 110 and 120 are driven in opposition (for example by a "push-pull" circuit) to cause motion in cuff 150. Drivers 170 and 175 are connected to a waveform generator 185 which creates a repetitive (either cyclic or pseudo-random) signal (see FIG. 3 for exemplary waveforms). The period and amplitude and pattern of the signal from waveform generator 185 are controllable to maximize release of dopamine during a therapeutic session.

Figure 2:
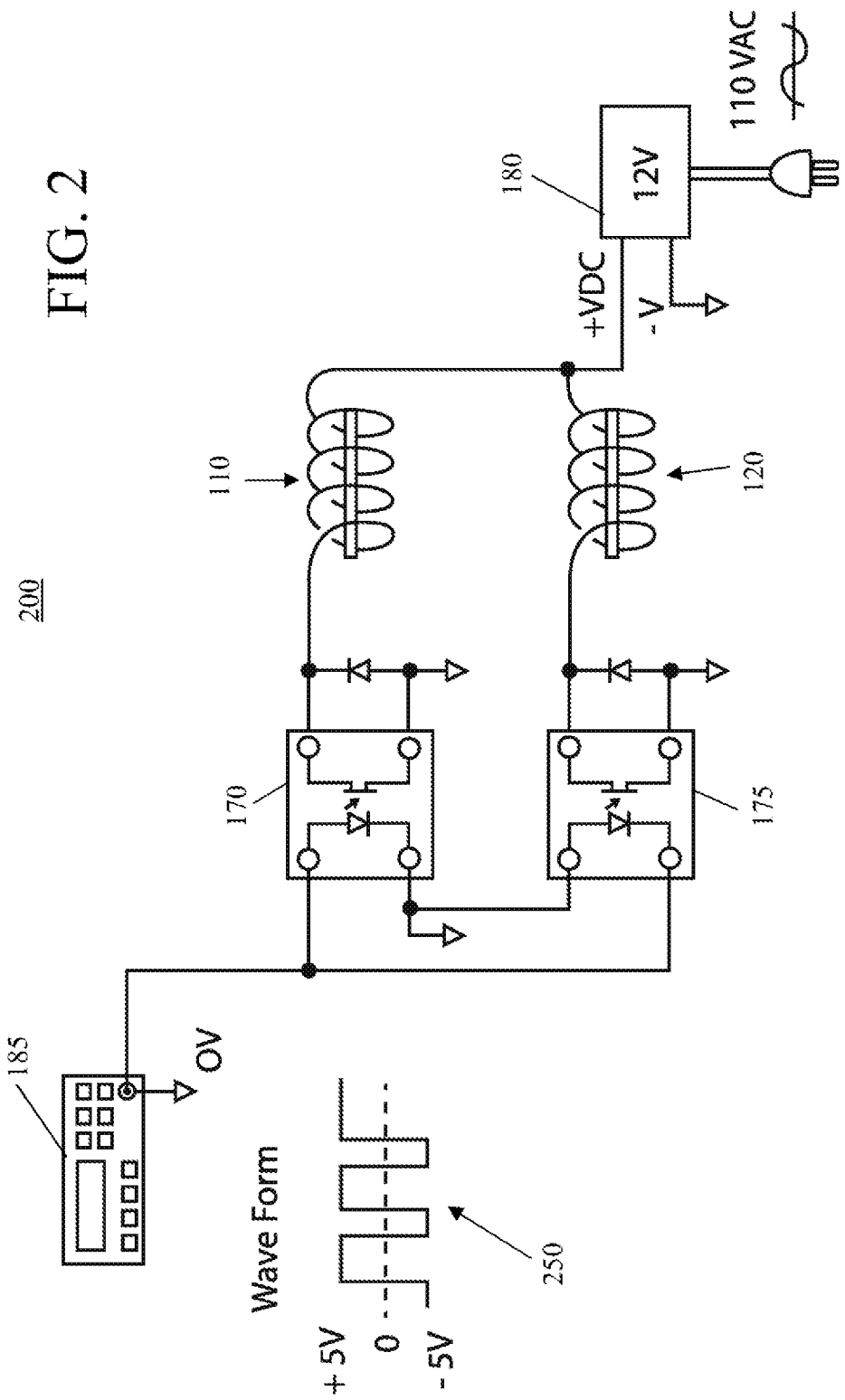
FIG. 2 is a circuit diagram for the control and drive system of the apparatus of FIG. 1.

FIG. 2 is a circuit diagram of device 100, wherein waveform generator 185 provides an input to opto-isolators 170 and 175 (for example, in the form of waveform 250), which in turn drive solenoid actuators 110 and 120. Power supply 180 110 VAC to 12 VDC to power the operation of actuators 110 and 120.

The opto-isolated circuit shown in FIG. 2 has the advantage of saturated switching which uses less power, but causes full articulation of the patient's hand. In the alternative, a linear circuit can be used to replace the saturating circuit. The controllable waveform generator 185 can be set to use other waveforms such as sinusoidal or triangle whereby both amplitude and period can be varied. This will cause smoother, yet sporadic, hand motion. It is understood that waveform generator 185 may be any suitable signal generation circuit and need not be a stand-alone function generator.

Figure 4:
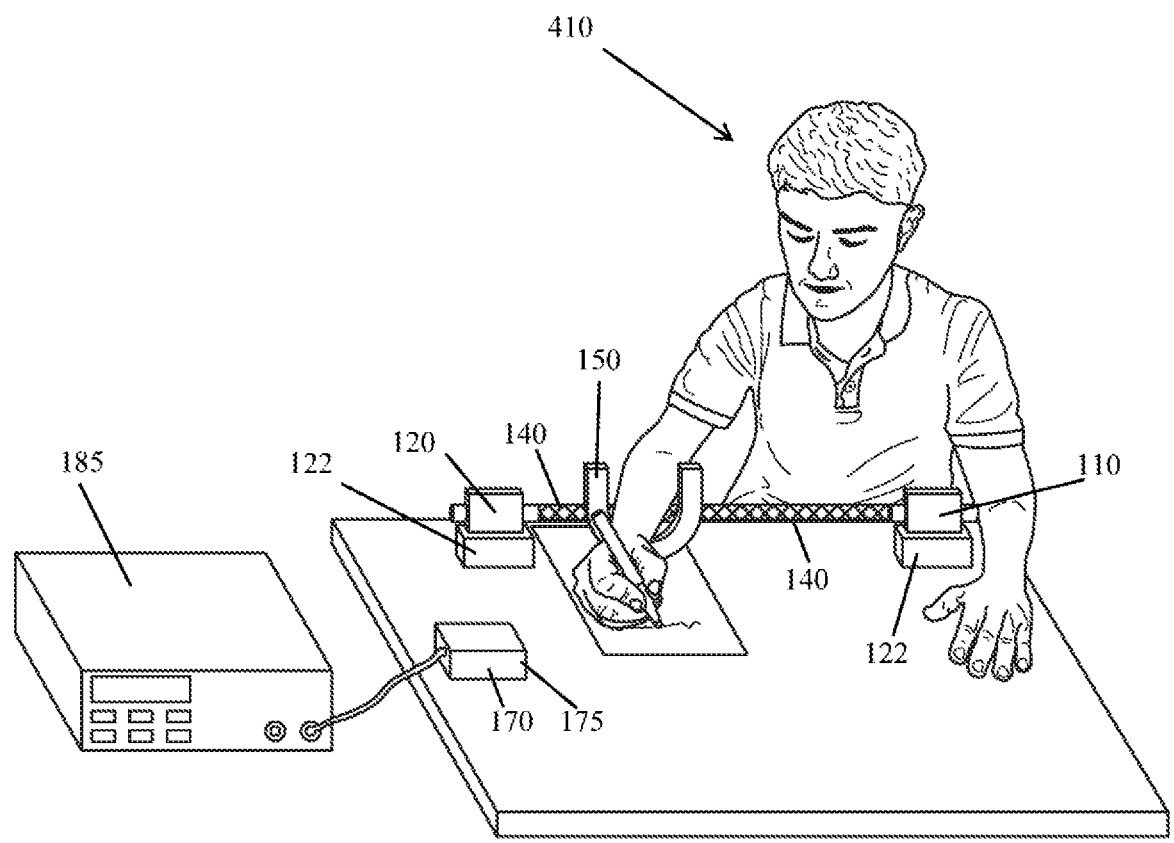
FIG. 4 depicts an individual using the apparatus of FIG. 1.
Figure 5:
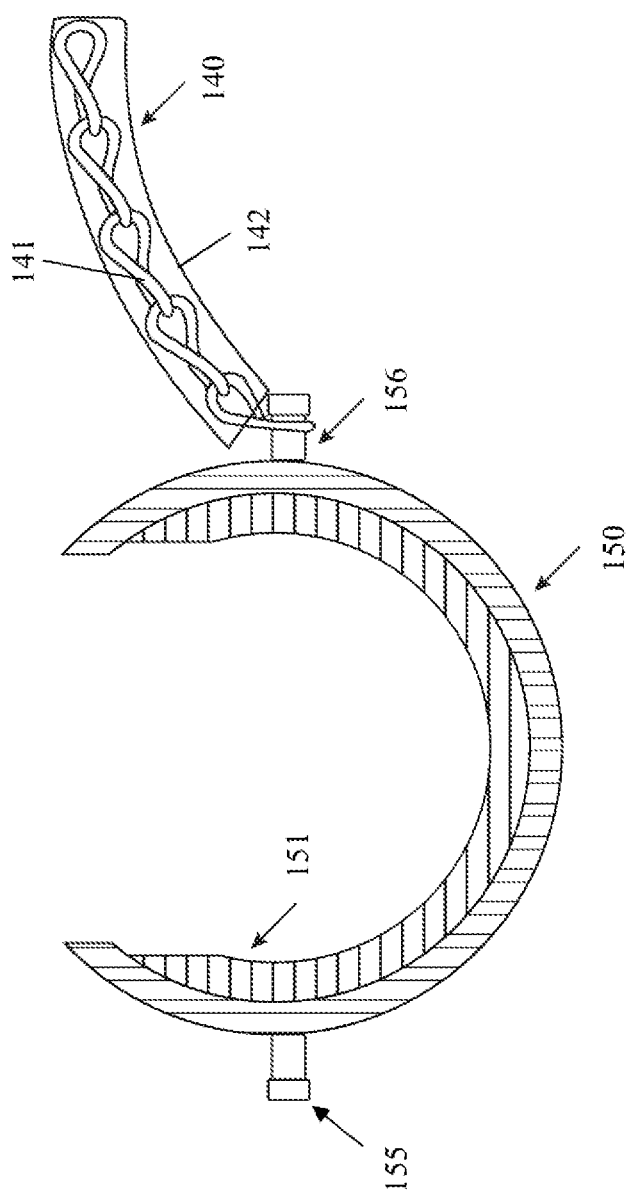
FIG. 5 shows a detailed drawing of the cuff and connector of the apparatus of FIG. 1.

FIG. 4 depicts a person 410 placing their hand inside of cuff 150 and attempting to perform a basic manual task (such as writing) while device 100 is in operation. When person 410 places his or her hand inside the cuff 150 and the device 100 is activated, the hand of person 410 is tugged gently side to side in sporadic movement. This movement is meant to replicate tremors.

During an exemplary therapy session, the patient 410 is given a simple repetitive task requiring fine motor skill and hand eye coordination such as writing their name. In an embodiment, the signal generator 185 generates a pattern which is pseudo randomized with the goal of maximizing the release of dopamine (see, e.g., waveform C on FIG. 3). It is speculated that, since the patient's brain cannot reliably predict the required compensating motion during therapy with the machine, the "error result" (predicted vs actual) will not drive to zero and dopamine will continue to be produced during therapy.

It is speculated that a further improvement could include a real-time scan (e.g., Dopascan or DaTscan) used to estimate dopamine release to form a feedback mechanism to adjust the controllable waveform generator to maximize the release of Dopamine.

A further improvement to this proposed therapy would include the step of surgical implantation of stem cells in the substantia nigra. The patient would then be given therapy from the device 100 to help insure that those cells differentiate and successfully wire into local nigra circuitry. It is necessary for the survival of a newly inserted neuron that it become connected and active in local neural circuitry. It is speculated that the therapy would help insure those local connections would form and fire in synchronization, thereby helping the new dopamine producing neurons survive.

It is speculated that a further improvement could include a real-time scan to estimate neural firing activity in the substantia nigra, where the results of said scan form a feedback mechanism to adjust the controllable waveform generator to maximize the firing of those neurons to help insure that the newly formed neurons integrate into local dopamine releasing circuitry.

In addition, Parkinson's disease has numerous symptoms including tremors in the hand, while the Essential Tremor is a disease that is mainly associated with the tremors that it causes. There are many differences between the two diseases. For instance, Essential Tremor is mainly a genetic disorder, while the cause of Parkinson's is unknown. Because of the differences in symptoms of said diseases, the treatments for these diseases are very different. The disclosed invention also simulates the two different types of handwritings that can be found in Parkinson's patients and Essential Tremor patients. This is accomplished by setting the controllable waveform to either 9-10 Hz or 5-6 Hz, which cause the machine to simulate physiological tremor and PD tremor, respectively.

These two modes can be changed so that when a person attempts to write their name on a piece of paper, the difference between the two handwritings is readily distinguishable between Parkinson's and Essential Tremor. Being able to recognize the specific qualities of a person's tremor through their handwriting could help medical practitioners to more readily identify and diagnose those different neurological diseases.

Further, the person learning about the diseases will be able to experience firsthand how it would feel to have one side effect of this terrible disease. In focus group testing, those who experiencing simulated tremors caused by the machine, reported a 78% increased connection (empathy) with a Parkinson's sufferer.

Figure 6:
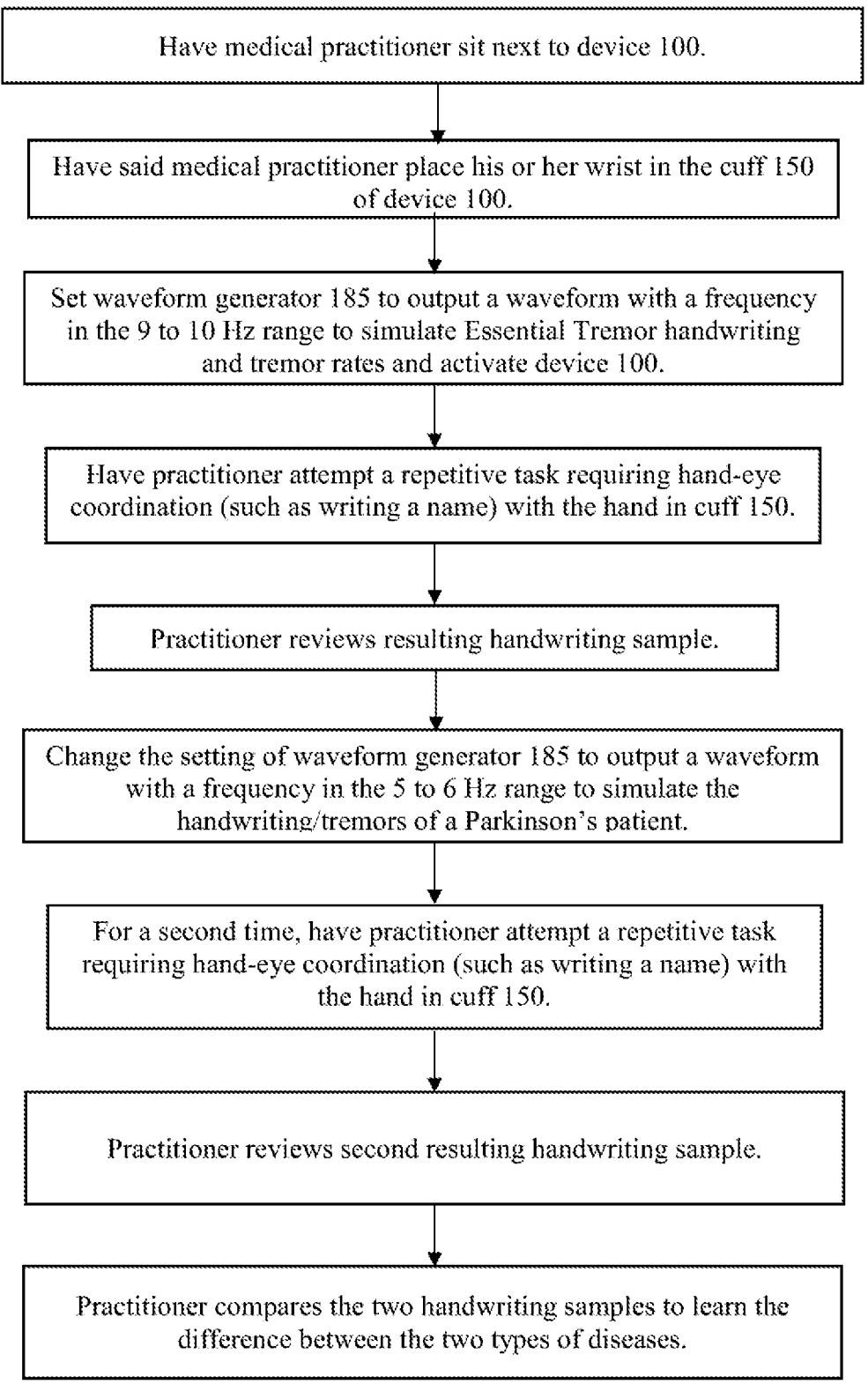
FIG. 6 is a flow chart describing a proposed training plan for medical practitioners who might use the apparatus of FIG. 1.

FIG. 6 is a flow chart outlining suggested steps in the training of a medical practitioner to learn to distinguish between Parkinson's disease and Essential tremor using device 100, said steps including: having a medical practitioner sit next to device 100; having said medical practitioner place his or her wrist in the cuff 150 of device 100; setting the waveform generator 185 to output a waveform with a frequency in the 9 to 10 Hz range to simulate Essential Tremor handwriting and tremor rates and activating device 100; instruct said medial practitioner to write their name on a piece of paper in front of them using the wrist in cuff 150; instructing practitioner to review the resulting handwriting; changing the setting of the waveform generator 185 to output a waveform with a frequency in the 5 to 6 Hz range to simulate the handwriting/tremors of a Parkinson's patient; again instruct said medial practitioner to write their name on a piece of paper in front of them using the wrist in cuff 150; again instructing the practitioner to review the resulting handwriting; instructing the practitioner to compare the two handwriting samples and learn the difference between the two types of diseases.

Figure 7:
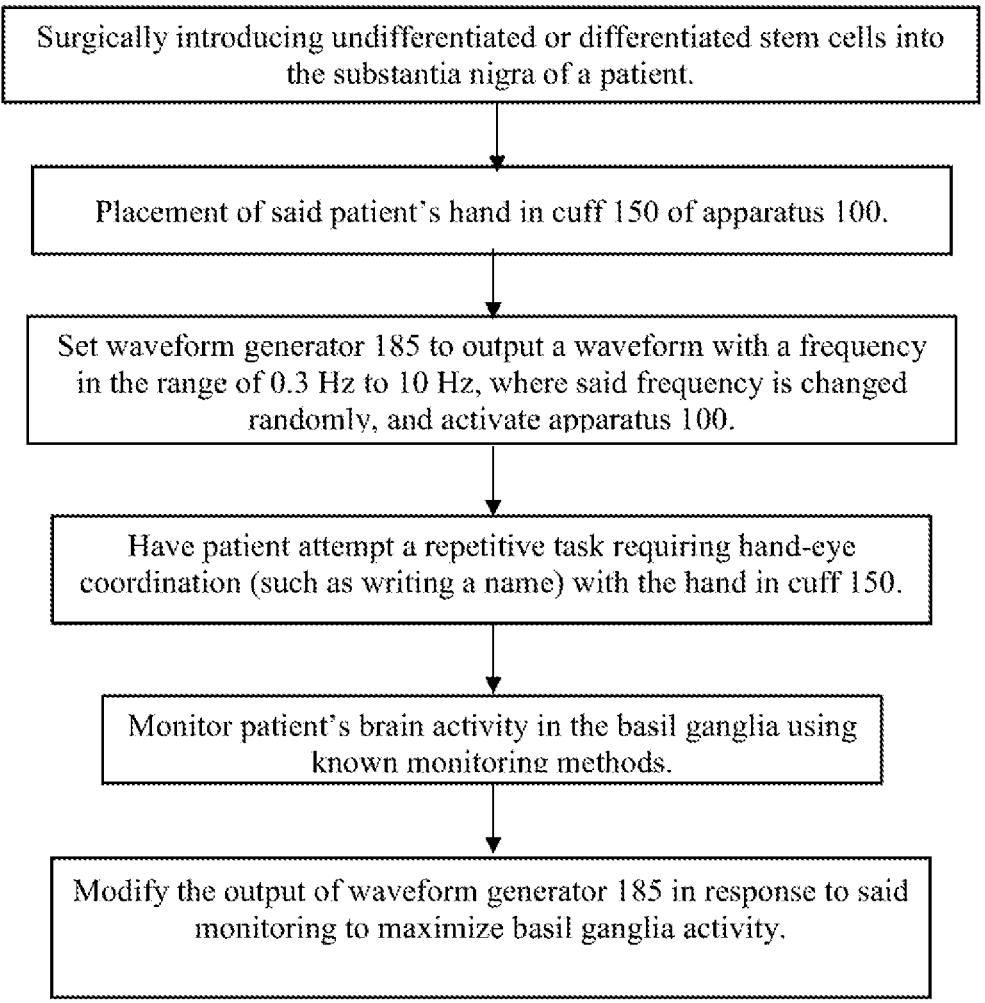
FIG. 7 is a flow chart describing a proposed therapeutic plan employing the apparatus of FIG. 1 in connection with certain speculative surgical therapies.

FIG. 7 is a flow chart outlining suggested steps in a proposed therapy using device 100 to be employed in combination with certain surgical therapies, said steps including: surgically introducing undifferentiated or differentiated stem cells into the substantia nigra of a patient; patient subsequently engaging in physical therapy to cause the new neurons to become integrated into the local circuits of the substantia nigra, said physical therapy comprising repetitive hand/eye coordinated tasks such as the physical application of a reciprocating opposing force by device 100 to perturb the patient's hand motion based on a waveform generated by a controllable waveform generator 185; monitoring of said patient's brain activity in the basil ganglia; modifying the output of waveform generator 185 in response to said brain activity monitoring to maximize basil ganglia activity.

What is claimed is:

1. An apparatus for simulating hand tremors comprising:
a waveform generator operable to output a waveform;
an electric driver connected to said waveform generator, wherein said electric driver is operable to receive as an input said waveform, and wherein said electric driver outputs a drive signal, wherein said drive signal varies in response to changes in said waveform;
an actuator comprising a connection point attached thereto the actuator, wherein said actuator is connected to said electric driver, wherein said actuator is operable to receive as an input said drive signal, and wherein said actuator is operable to mechanically drive and displace said connection point along an axis in response to said drive signal;
a cuff configured to encircle a portion of a human hand or arm; and
a semi-rigid connecting mechanism extending between said connection point and said cuff, the semi-rigid connecting mechanism attached on one end thereof to said connection point of the actuator and attached on an opposing end thereof to said cuff; wherein operation of said actuator displaces said connection point, said connecting mechanism, and said cuff along said axis.

2. The apparatus of claim 1, wherein said waveform generator is operable to modify said waveform to cause the displacement of said cuff to simulate hand tremors symptomatic of Essential Tremor disease or Parkinson's disease, wherein the actuator is configured to produce for the displacement randomized stroke length displacements.

3. The apparatus of claim 1, wherein said waveform has a frequency in the range of 5 Hz to 6 Hz.

4. The apparatus of claim 1, wherein said waveform has a frequency in the range of 9 Hz to 10 Hz.

5. The apparatus of claim 1, wherein said waveform has randomized frequency in the range of 0.3 Hz to 10 Hz.

6. The apparatus of claim 1, wherein said actuator is an electromagnetic actuator, a pneumatic actuator, a reciprocating motor, or a voice coil.

7. The apparatus of claim 3, wherein said electric driver is an opto-isolator, a transistor protected by a fly-back diode, or a relay.

8. The apparatus of claim 1, wherein said semi-rigid connecting mechanism is comprised of one or more of a metallic chain link chain, a metallic chain link chain encased in partially elastic plastic, a length of partially elastic plastic or rubber, and a sliding rail.

9. The apparatus of claim 1, further comprising:
a second electric driver connected to said waveform generator, wherein said second electric driver is operable to receive as an input said waveform, and wherein said second electric driver outputs a second drive signal, wherein said second drive signal varies in response to changes in said waveform;
a second actuator opposing the first actuator and comprising a second connection point, wherein said second actuator is connected to said second electric driver, wherein said second actuator is operable to receive as an input said second drive signal, and wherein said second actuator is operable to displace said second connection point along said axis in response to said second drive signal; and a second semi-rigid connecting mechanism attached to said second connection point and to
said cuff;
wherein operation of said second actuator displaces said cuff along said axis.

10. The apparatus of claim 9, wherein said second drive signal is the inverse of said drive signal, and wherein operation of said actuator and said second actuator in response to said drive signal and said second drive signal synchronously displace said connection point and said second connection point in a same direction along said axis.

11. The apparatus of claim 6, wherein said actuator is a solenoid and said second actuator is a solenoid.

12. An apparatus for providing physical therapy to an individual, said apparatus comprising:
a waveform generator operable to output a waveform;
an electric driver connected to said waveform generator, wherein said electric driver is operable to receive as an input said waveform, and wherein said electric driver outputs a drive signal, wherein said drive signal varies in response to changes in said waveform;
an actuator comprising a connection point attached thereto the actuator, wherein said actuator is connected to said electric driver, wherein said actuator is operable to receive as an input said drive signal, and wherein said actuator is operable to drive and displace said connection point along a linear axis in response to said drive signal;
a cuff configured to encircle a portion of a hand or arm of said individual, wherein operation of said actuator displaces said connection point and said cuff along said linear axis;
a semi-rigid connecting mechanism extending between said connection point and said cuff, the semi-rigid connecting mechanism attached on one end thereof to said connection point of the actuator and attached on an opposing end thereof to said cuff;
means for monitoring a dopamine level of said individual when said individual's hand or arm is placed inside of said cuff and said apparatus in in operation, wherein said monitoring means generates a monitoring means output; and
a control system connected to said monitoring means, wherein said monitoring means output is an input to said control system, wherein said control system is connected to said waveform generator, and wherein said control system is operable to modify the amplitude and frequency of said waveform to maximize said dopamine level of said individual during use of said apparatus.

13. The apparatus of claim 12, wherein said actuator is an electromagnetic actuator, a pneumatic actuator, a reciprocating motor, or a voice coil.

14. The apparatus of claim 13, wherein said electric driver is an opto-isolator, a transistor protected by a fly-back diode, or a relay.

15. The apparatus of claim 14, wherein said connecting mechanism is comprised of one or more of a metallic chain link chain, a metallic chain link chain encased in partially elastic plastic, a length of partially elastic plastic or rubber, and a sliding rail.

16. The apparatus of claim 12, further comprising:
a second electric driver connected to said waveform generator, wherein said second electric driver is operable to receive as an input said waveform, and wherein said second electric driver outputs a second drive signal, wherein said second drive signal varies in response to changes in said waveform;
a second actuator comprising a second connection point, wherein said second actuator is connected to said second electric driver, wherein said second actuator is operable to receive as an input said second drive signal, and wherein said second actuator is operable to displace said second connection point along said axis in response to said second drive signal; and a second connecting mechanism attached to said second connection point and to said cuff;
wherein operation of said second actuator displaces said cuff along said axis.

17. The apparatus of claim 16, wherein said second drive signal is the inverse of said drive signal, and wherein operation of said actuator and said second actuator in response to said drive signal and said second drive signal synchronously displace said connection point and said second connection point in a same direction along said axis.

18. The apparatus of claim 16, wherein said actuator is a solenoid and said second actuator is a solenoid.

19. The apparatus of claim 1 as a therapeutic apparatus, said therapeutic apparatus further comprising:
means for monitoring a dopamine level of a patient who has had undifferentiated or differentiated stem cells surgically introduced into said patient's substantia nigra when said patient's hand or arm is placed inside of said cuff and said apparatus in in operation.

20. The apparatus of claim 19, further comprising:
a second electric driver connected to said waveform generator, wherein said second electric driver is operable to receive as an input said waveform, and wherein said second electric driver outputs a second drive signal, wherein said second drive signal varies in response to changes in said waveform;
a second actuator comprising a second connection point, wherein said second actuator is connected to said second electric driver, wherein said second actuator is operable to receive as an input said second drive signal, and wherein said second actuator is operable to displace said second connection point along said axis in response to said second drive signal; and a second connecting mechanism attached to said second connection point and to
said cuff;
wherein operation of said second actuator displaces said cuff along said axis.

21. The apparatus of claim 19, further comprising:
a control system connected to said monitoring means generating a monitoring means output, wherein said monitoring means output is an input to the control system, wherein said control system is connected to said waveform generator, and wherein the control system is operable to modify the amplitude and frequency of said waveform to maximize said dopamine level of said individual during use of said apparatus, wherein the control system is operable during the following steps of:
securing a wrist or arm of said patient into said cuff;
activating said apparatus such that said cuff exerts a reciprocating opposing force to said patient's hand;
instructing said patient to attempt a repetitive hand-eye coordinated task with said hand secured in said cuff;
monitoring said patient's dopamine levels using said monitoring means while said patient attempts said repetitive hand-eye coordinated task; and
modifying said waveform using said control system in response to said monitoring means output to maximize said patient's dopamine levels during said therapy session.

22. An apparatus for providing physical therapy, comprising:
a waveform generator operable to output a waveform;
an electric driver connected to said waveform generator, wherein said electric driver is operable to receive as an input said waveform, and wherein said electric driver outputs a drive signal, wherein said drive signal varies in response to changes in said waveform;
an actuator comprising a connection point attached thereto the actuator, wherein said actuator is connected to said electric driver, wherein said actuator is operable to receive as an input said drive signal, and wherein said actuator is configured to mechanically drive and displace said connection point along an axis in response to said drive signal;
a cuff configured to encircle a portion of a human hand or arm; and
a connecting mechanism extending between said connection point and said cuff, the connecting mechanism attached on one end thereof to said connection point of the actuator and attached on an opposing end thereof to said cuff,
wherein, via movement of the connection mechanism, movement of connection point by the actuator displaces said cuff along said axis.

* * * * *